United States Patent
Johnston, III

(10) Patent No.: US 7,591,817 B2
(45) Date of Patent: Sep. 22, 2009

(54) SURGICAL INSTRUMENT FOR TISSUE RESECTION AND DISSECTION

(75) Inventor: William K. Johnston, III, Chicago, IL (US)

(73) Assignee: NorthShore University HealthSystem Research Institute, Evanston, IL (US)

( * ) Notice: Subject to any disclaimer, the term of this patent is extended or adjusted under 35 U.S.C. 154(b) by 284 days.

(21) Appl. No.: 11/247,429

(22) Filed: Oct. 11, 2005

(65) Prior Publication Data

US 2007/0083196 A1   Apr. 12, 2007

(51) Int. Cl.
*A61B 18/18* (2006.01)
(52) U.S. Cl. .................................. 606/45; 600/374
(58) Field of Classification Search .................. 606/45, 606/48, 49, 50; 600/374
See application file for complete search history.

(56) References Cited

U.S. PATENT DOCUMENTS

| | | | |
|---|---|---|---|
| 4,026,300 A | | 5/1977 | DeLuca et al. |
| 4,027,674 A | | 6/1977 | Tessler et al. |
| 5,282,815 A | | 2/1994 | Kabbara |
| 5,810,805 A | | 9/1998 | Sutcu et al. |
| 5,980,563 A | | 11/1999 | Tu et al. |
| 6,022,362 A | | 2/2000 | Lee et al. |
| 6,033,397 A | * | 3/2000 | Laufer et al. .................. 606/27 |
| 6,280,441 B1 | | 8/2001 | Ryan |
| 6,325,797 B1 | * | 12/2001 | Stewart et al. ................. 606/41 |
| 6,453,906 B1 | * | 9/2002 | Taylor et al. .................. 128/898 |
| 6,471,709 B1 | | 10/2002 | Fawzi et al. |
| 6,529,778 B2 | | 3/2003 | Prutchi |
| 6,600,956 B2 | | 7/2003 | Maschino et al. |
| 6,733,499 B2 | * | 5/2004 | Scheib .......................... 606/41 |
| 6,972,016 B2 | * | 12/2005 | Hill et al. ...................... 606/41 |
| 2001/0053909 A1 | | 12/2001 | Nakada et al. |
| 2003/0045873 A1 | | 3/2003 | Hinchliffe |
| 2004/0199159 A1 | | 10/2004 | Lee et al. |
| 2005/0033314 A1 | | 2/2005 | Sakurai et al. |
| 2005/0149061 A1 | | 7/2005 | Brassel |

OTHER PUBLICATIONS

International Search Report and Written Opinion for international application No. PCT/US06/39634 (Jan. 8, 2008) (8 pages).

* cited by examiner

*Primary Examiner*—Michael Peffley
(74) *Attorney, Agent, or Firm*—Marshall, Gerstein & Borun LLP

(57) ABSTRACT

A surgical instrument has a shaft with a longitudinal axis, a proximal end, and a distal end. The shaft is rotatable about its longitudinal axis by user manipulation of the proximal end. A tissue retainer is positioned at the distal end and is rotatable with the shaft. The retainer has a curved portion that extends around a retainer axis, a tissue holding space within the curved portion, and an entry opening into the holding space. The retainer is configured to be received over and at least partly circumvent a target structure of a surgical field received in the holding space via the entry opening. A surgical component is positioned on a portion of the retainer laterally offset from both the retainer axis and the holding space, is rotatable with rotation of the shaft and retainer and is selectively energizeable to dissect selected tissue.

14 Claims, 4 Drawing Sheets

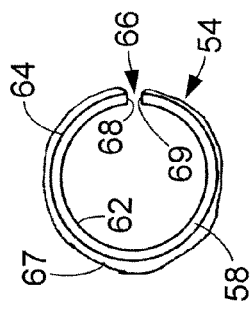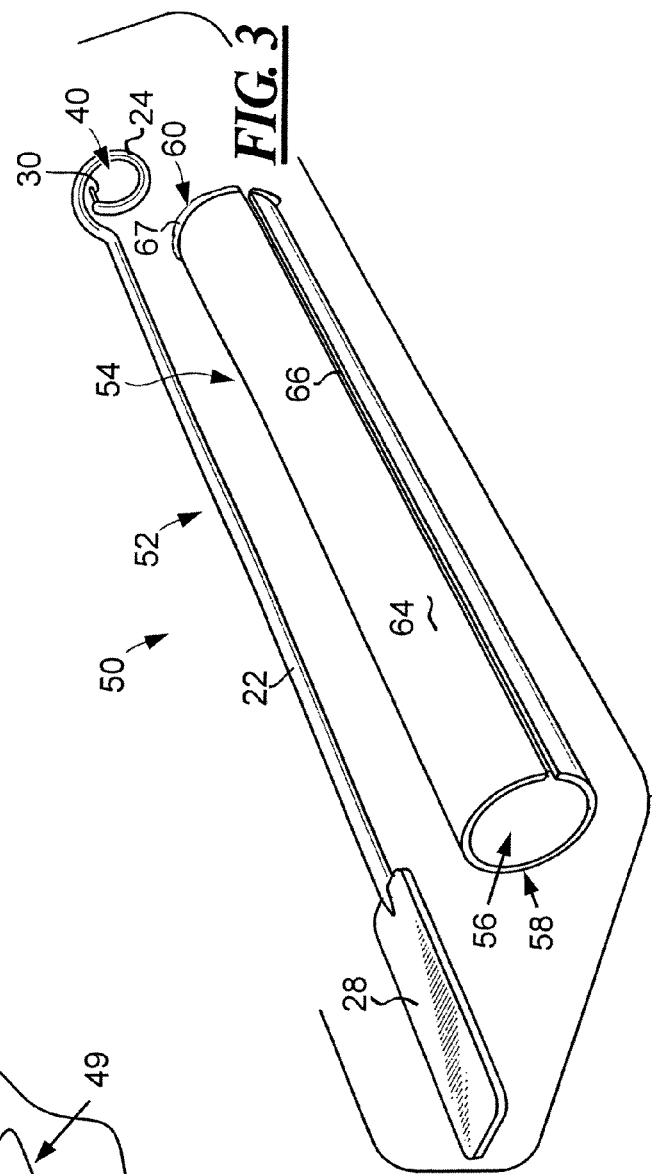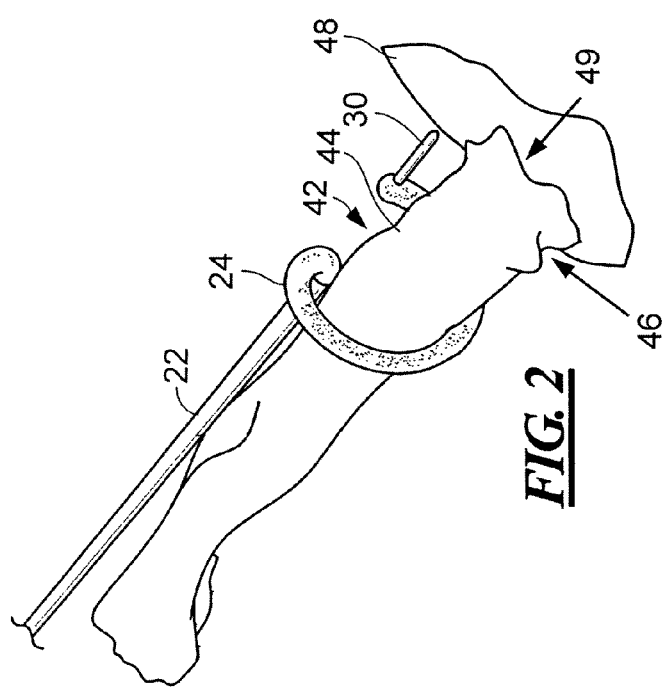

SURGICAL INSTRUMENT FOR TISSUE RESECTION AND DISSECTION

BACKGROUND OF THE INVENTION

1. Field of the Disclosure

The present disclosure is generally directed to surgical instruments and method, and more particularly to a surgical instrument and method of tissue resection and dissection.

2. Description of Related Art

Surgeons often perform procedures where bodily structures must be separated from surrounding tissue. Some of these structures are relatively thin, elongate structures such as tendons, veins, nerves, arteries, and the like. Separation at the juncture between the structure and the adjacent tissue is often desirable, but can very often be somewhat technically difficult and time consuming.

For example, urothelial carcinoma of the upper urinary tract is more commonly known simply as cancer of the kidney lining or of the ureter, which is the tube that drains the kidney to the bladder. This type of cancer accounts for about 4.5 to about 9% of all renal tumors and about 5 to 6% of all urothelial tumors. The traditional or standard treatment for this type of cancer is nephroureterectomy. The procedure essentially involves removal of the kidney and ureter along with excision of the distal ureter from the bladder, along with the small surrounding bladder material or bladder cusp removed with the ureter's opening in the bladder.

Laparoscopy, which involves operating through small ports or incisions and use of cameras, has been applied increasingly in many. of these types of procedures, including nephroureterectomy. As urological surgeons become more comfortable with hand-assisted laparoscopy (laparoscopic surgery in which one hand is inserted through a hand assist port to aid with the surgery), minimally invasive approaches to nephroureterectomy or treatment of this type of cancer have become more commonly employed. However, it remains difficult to manage dissection of the distal ureter or bladder cusp even with these more advanced techniques. This step is the most difficult and time-consuming task during laparoscopic urothelial procedure. Also, other difficulties can arise during resection of the distal ureter, such as extravasation of bladder irrigation, i.e., urine leakage to surrounding tissues. This may lead to hyponatremia, a low sodium condition, or hypervolumeia, a fluid overload condition.

A number of existing options are known for managing the distal ureter during surgery, whether using laparoscopic procedures or not. One option is a complete open bladder cuff removal, which is time consuming and requires a large incision and opening of the bladder. Another option is transurethral resection with a Collin's knife, which requires operating up through the urethra tube leading to the bladder. Transurethral resection is also relatively time consuming and requires repositioning of the patient during the procedure. Another option is transvesical port replacement and resection using a Collin's knife, which requires placing a working or laparoscopic port directly into the bladder. Transvesical port replacement is less time consuming but can be technically very difficult to perform. Another option is stapling of the distal ureter, which poses some degree of risk of cancer recurrence in the intramural ureter left behind in the patient. Each of the above optional procedures is routinely practiced and all result in extravasation of urine into the surrounding area. However, they are all accepted options and provide optimal oncological outcomes, which is to ultimately eliminate the existing cancerous tissue.

BRIEF DESCRIPTION OF THE DRAWINGS

Objects, features, and advantages of the present invention will become apparent upon reading the following description in conjunction with the drawing figures, in which:

FIG. 2 shows a fragmentary perspective view of the surgical instrument shown in FIG. 1 and during a surgical procedure.

FIG. 3 shows a perspective view of another example of a surgical instrument constructed in accordance with the teachings of the present disclosure.

FIG. 4 shows an end view of the protective or insulating sheath component of the surgical instrument shown in FIG. 3.

DETAILED DESCRIPTION OF THE DISCLOSURE

The present disclosure is for surgical instruments and methods that improve upon or eliminate the above noted and other problems associated with prior known instruments and procedures. The disclosed instrument examples can be used either during open surgery or during a laparoscopic or minimally invasive procedure. The disclosed devices can be utilized to complete resection of the surrounding tissue along a target structure while preserving the integrity of the structure or other tissue of interest. The disclosed instruments also can be used to resect tissue along a ureter and to dissect the bladder cusp of the ureter or other tissue of interest. The disclosed instruments can utilize blunt dissection and/or electrocautery dissection using a monopolar or bipolar electrodes. The instruments can also optionally use laser, radio frequency (RF), microwave, ultrasound, or other surgical component energy sources. The instruments disclosed herein can be used in an antegrade or retrograde manner through a port used during laparoscopic surgery. The surgical instruments disclosed herein can be placed through a port or can be placed into the abdomen through a hand port during hand-assisted laparoscopy prior to passing the narrow handle back out of the laparoscopic port. If use in a retrograde manner, the instrument would work through a port placed into the bladder.

Figure 1:
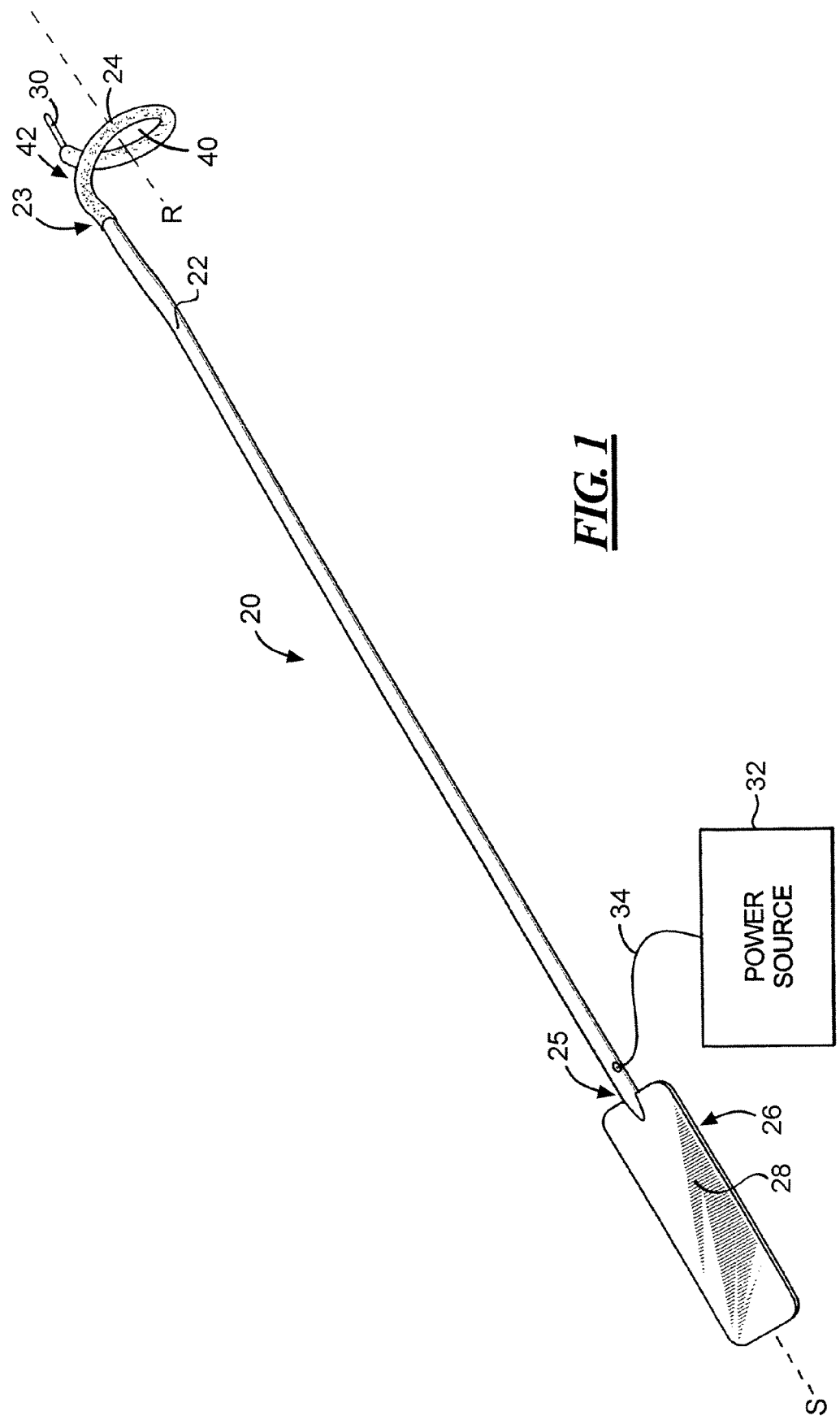
FIG. 1 shows a perspective view of one example of a surgical instrument constructed in accordance with the teachings of the present disclosure.

Turning now to the drawings, FIGS. 1 and 2 illustrate one example of a surgical instrument 20 constructed in accordance with the teachings of the present disclosure. In this example, the instrument 20 has an elongate rod or shaft 22 with a distal or working end 23. In this example, the working end terminates at a tissue retainer 24 described in greater detail below. The shaft 22 also has a proximal end 25 opposite the distal end defining a handle or grip end 26 for manipulation by a user.

The handle or grip end 26 can be configured in any suitable manner and can include complex ergonomic features or simple forms and/or contours that assist a surgeon in handling and manipulating the instrument 20. In this example, the handle or grip end 26 is shown to include a thin, relatively wide paddle 28. However, other examples may include more elaborate grips configured to be gripped by a surgeon's hand or palm, or to be gripped between only a thumb and forefinger. In one example, a simple ball of greater diameter than the shaft 22 can be provided on the proximal end 25 of the shaft as a substitute for the paddle 28.

The instrument 20 in this example also includes a surgical component 30 at the working or distal end 23. In this example, the surgical component 30 is provided as a distal extension of the tissue receiver 24 carried on the distal end 23 of the shaft.

Also as shown in FIG. 1, a power or energy source is coupled to the instrument 20 to selectively energize the surgical component 30. The energy source is schematically illustrated as power source 32 in FIG. 1. The power source 32 is coupled to the shaft 22 by one or more wires, leads, fibers, or the like. In the example shown in FIG. 1, the power source 32 is representative of any number of devices that can energize the surgical component 30. In one example, the surgical component 30 can be a simple monopolar electrode extending from the working end or tissue receiver. The lead can be a wire 34 connected directly to a solid metallic shaft 22. The power source 32 can be an electrical energy source that delivers a current to the shaft and thus to the electrode 30. In this example, the entire length of the shaft 22 can be insulated except for the exposed electrode 30. Thus, the electrode 30 will be "hot" when current flows from the source 32 through the shaft to the electrode 30. In such an example, the shaft 22 can be insulated simply so that no current touches or affects tissue in contact with the shaft 22, other than the electrode 30, during a surgical procedure. The "hot" end may be incorporated into an outer sheath of the instrument while utilizing an inner protective sheath to protect adjacent tissue as discussed below.

As will be evident to those having ordinary skill in the art, other energy sources and surgical component configurations are possible without departing from the spirit and scope of the present invention. The instrument shown in FIG. 1 is intended to be used in direct contact with a target tissue or structure. Thus, in this example, the tissue retainer 24 at the distal end 23 of the shaft 22 has a thicker insulating and protective material around all of its surfaces, leaving only the surgical component or electrode 30 exposed. To activate the power source, an actuator (not shown) can be provided as is known in the art. Actuator examples can include a foot pedal, a finger trigger, an on/off push button, or the like. The actuator can be provided either remote from the instrument 20, such as a foot pedal, or on or near the grip end 26 of the instrument, such as a button.

As shown in FIGS. 1 and 2, the tissue retainer 24 in one example is formed as a helical or spiral wire coupled to the working end 23 of the shaft 22. This helical or curved retainer is configured to define a tissue holding space 40 within and along the helix interior. In this example, as shown in FIGS. 1 and 2, the shape of the curved tissue retainer 24 creates an entry opening 42 into the tissue holding space 40. The helical contour of the wire retainer 24 extends around and generally in a direction along a longitudinal axis 'S' of the shaft as it circumvents the tissue holding space 40.

The helical tissue retainer 24 in this example defines a retainer axis 'R' positioned central to the tissue holding space 40. In this example, the retainer axis is offset from, but generally parallel to, the shaft longitudinal axis 'S' as shown in FIG. 1 and evident in FIG. 2. The tissue retainer 24 can be received over and at least partially circumvent a target structure 44 to be received in the tissue holding space 40 after insertion through the entry opening 42. In one example, the curved helical or spiral shape of the retainer 24 extends through about a 360° angle as depicted in FIG. 2. In other examples, the tissue retainer 24 can extend through angles less than, or even greater than, 360°. However, it may in many instances be preferable that the retainer 24 be shaped to at least extend more than 180° around the target structure 44 so that when the structure is captured in the holding space 40, the retainer does not slip off of that structure.

Also as depicted in FIGS. 1 and 2, the surgical component 30 in this example is aligned with and extends generally along the longitudinal axis 'S' of the shaft. This is so that the component does not readily excise tissue held in the space 40, but instead only contacts and excises tissue outward of the holding space and forward of the retainer 24. In other examples, the retainer axis 'R' of the tissue holding space 40 could be more closely aligned with the shaft axis. In such an example, the surgical component 30 is positioned laterally offset from both the longitudinal axis 'S' of the shaft and the retainer axis 'R' of the tissue holding space 40. Relative offset among these perimeters is preferred so that the surgical operation can be performed adequately as described below. Having the shaft axis and retainer axis offset laterally renders it easier to connect the instrument to the target structure with the shaft positioned adjacent the target structure for easier manipulation. In still other examples, the shaft axis 'S' and retainer axis 'R' need not be parallel, but can instead be oriented at an angle relative to one another. The particular structure and arrangement can be varied to accommodate a specific intended surgical use, if needed.

The instrument 20 shown in FIG. 1 can be used in either an open surgery or a laparoscopic procedure. If used in a laparoscopic environment, a small incision is cut to insert a tube or port (not shown) into which the instrument 20 is inserted. The laparoscopic port and other components are not shown herein; as they are well know in the art. A typical laparoscopic tube or port has about a 15 millimeter maximum diameter or less, so the disclosed instrument examples should be sized to accommodate if intended for use in laparoscopic procedures. Once an open incision, or once a laparoscopic incision is made and the port inserted, the instrument 20 can be manipulated in place with the tissue retainer 24 and the distal or working end 23 of the instrument adjacent the target structure 44 in the patient.

The entry opening 42 is then positioned facing the structure 44. The structure is passed through the opening 42 into the tissue holding space 40 with the shaft 22 positioned somewhat parallel to the structure 44 in this example. The surgeon can then move or guide the instrument along the structure. Tissue resection can be performed simply by blunt resection, i.e., by positive forward pressure applied by moving the instrument and retainer along the target structure 44. If needed, the surgical component 30 can be selectively energized to assist in resection while moving the instrument along. Also if needed, the shaft 22 can be rotated while energizing the component 30 and/or while moving the instrument along the structure. This may assist in tissue resection. Once a target tissue to be dissected is positioned adjacent the structure 44 distal end, the shaft 22 can be further rotated while energizing the component 30, which in turn cuts the target tissue.

The example of a nephroureterectomy procedure noted above is used to generally remove the entire ureter, which is the target structure 44, either with or without a portion of the kidney. Once the proximal end of the ureter adjacent the kidney is removed or separated from other bodily tissue, the instruments disclosed herein are particularly useful for dissecting the ureter at the bladder cusp.

To perform a nephroureterectomy procedure using the instrument illustrated in FIGS. 1 and 2, the instrument 20 is manipulated so that the tissue retainer 24 is placed adjacent a target ureter 44. The cancerous ureter 44 is received in the tissue holding space 40 through the entry opening 42 in the retainer. The retainer 24 then can be manipulated to guide and move the instrument 20 along the ureter structure. The retainer itself can perform blunt tissue resection separating the ureter exterior from any loosely entangled surrounding tissue. Tissue resection can also be performed by energizing the surgical component 30 and rotating the instrument 20 as necessary to separate any surrounding tissue from the ureter.

As depicted generally in FIG. 2, the dissection procedure involves separating the distal ureter 46 of the ureter structure 44 from the bladder. In this example, the ureter is connected to the bladder 48 at a bladder cusp 49. The disclosed instrument 20 can be utilized to separate the bladder cusp 49 from the bladder 48 by electrocauterization while the cusp remains attached to the ureter 44. The surgical component 30 is energized as the shaft 22 is rotated. The offset between the position of the surgical component 30 and the retainer axis 'R' of the tissue holding space 40 creates circumferential movement of the component 30 around the exterior of the ureter to cut and cauterize simultaneously. During the resection and dissection steps, the thick insulation on the retainer 24 in this example helps to protect the ureter 44 from damage and also can insulate the ureter from electrical current or other energy passing through the shaft 22 to the surgical component 30. It is desirable in such a procedure to avoid any ureter tissue from being unintentionally dissected and left in the patient.

Figure 7:
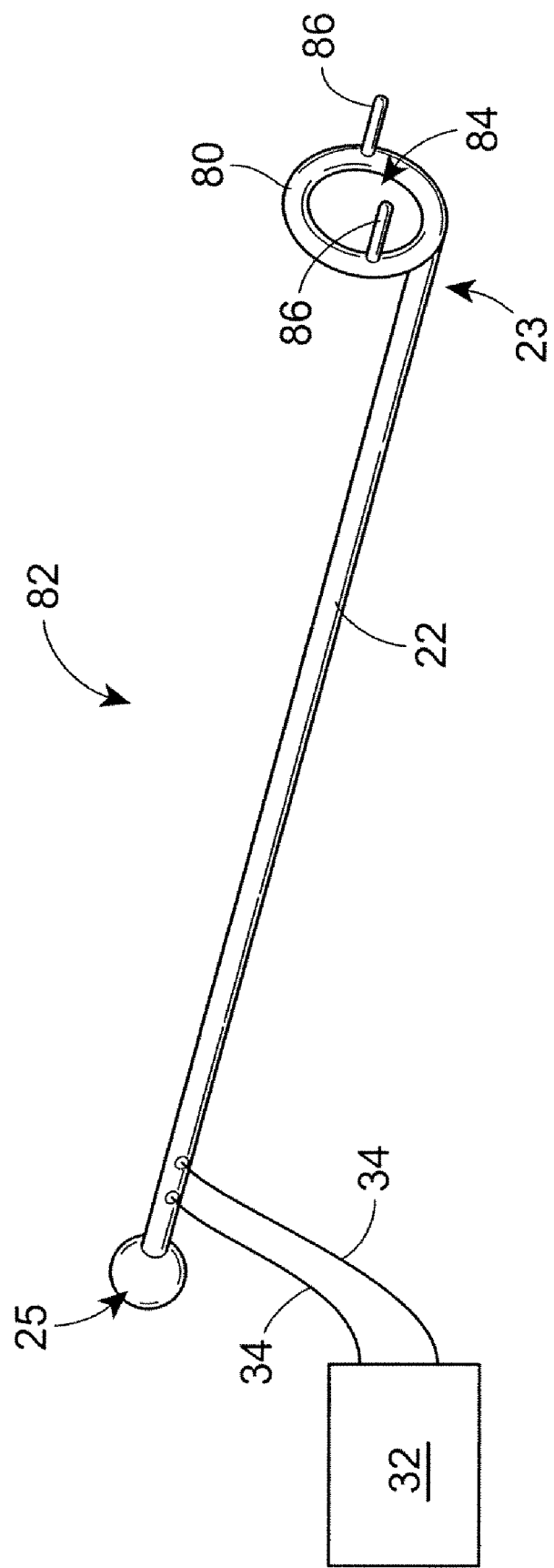
FIG. 7 shows a perspective view of another example of a surgical instrument constructed in accordance with teachings of the present disclosure.

The surgical component 30 disclosed herein can vary considerably and yet fall within the spirit and scope of the present invention. In the disclosed example shown in FIGS. 1 and 2, the surgical component 30 is a simple monopolar electrode that is left uninsulated. When current from the source 32 is passed through the shaft 22 to the uninsulated electrode 30, the electrode is "hot" and will simultaneously separate tissue and cauterize the exposed tissue left behind. In another example, the surgical component 30 can embody a bipolar, dual electrode configuration. In such an example (see FIG. 7 below), a pair of circumferentially opposed electrodes are provided on a part of the retainer. Current can be supplied from one wire to one of the electrodes, creating an arc across to pair of electrodes through the target tissue, and then return from the other electrode through a second wire.

As noted previously, the surgical component 30 can also become "hot" via an alternative energy source or power source 32. In one example, the component 30 can be a laser emitting tip, a RF emitting tip, an ultrasound emitting tip, a microwave emitting tip, or the like. The power source 32 can be suitably provided to deliver the desired type of energy. The shaft 22 in one disclosed example can be a solid metallic material to accommodate the monopolar example shown in FIG. 1. However, the shaft can be a thin walled, hollow material through which wires, fibers, or the like can extend from the power source 32 to the surgical component 30.

Another embodiment is illustrated in FIG. 3. In this example, a surgical device 50 is depicted and includes a surgical instrument 52 substantially similar in construction to the previously described instrument 20. However, the exterior surfaces of the retainer 24 on the distal or working end 23 need not be provided with a thicker insulation surrounding its exterior surfaces. Instead, the working end 23 can be covered or insulated merely to the same degree that the shaft 22 is insulated. The disclosed device 50 instead includes a secondary, discrete insulating or protective sheath 54. The sheath 54 is preferably formed from a material that is non-conductive of electrical or other energy. Thus, the sheath 54 can protect the structure 44 from energy, such as electrical current, passing through the instrument 52. In this example, the sheath 54 is formed as an elongate tube having a longitudinal axis 'A' and an opening 56 extending lengthwise through and along the longitudinal axis. The opening 56 extends from one end 58 of the sheath to its opposite end 60. The sheath includes an interior surface 62 that defines the opening 56 and an exterior surface 64 that faces outward.

During use, the sheath 54 is received around a structure to protect the structure while resection and dissection procedures are conducted. In this example, the elongate tubular sheath 54 includes a longitudinal slit 66 extending along the entire length of the sheath. If formed from an insulating plastic or other semi-flexible material, the sheath can simply be opened to create a gap between the edges 68 and 69 facing the slit 66 so that the structure 44 can be inserted into the opening 56.

During a surgical procedure, the sheath 54 can be inserted adjacent a target structure either through an open incision, a hand-assist port, or a laparoscopic port. Once installed, the sheath 54 can be hand installed over the target structure 44 via the open incision, or remotely installed utilizing additional tools through the laparoscopic orifice or port.

In one example, the sheath 54 is particularly useful during the nephroureterectomy procedure. The elongate sheath 54 can be spread open and installed over the ureter of a patient with the ureter borne against the interior surface 62 of the sheath. The retainer 24 of the instrument 52 can then be inserted via the entry opening 42 over the exterior surface 64 of the sheath. The sheath protects the ureter from damage as the instrument 52 is guided along the ureter during resection or dissection of tissue surrounding the ureter. The proximal portion of the ureter can first be dissected free from surrounding structures to allow placement of the insulating sheath 54 on the ureter. The distal end of the insulating sheath can have a widened distal tip or annular stop 67 (see FIGS. 3 and 4) to prevent the retainer 24 or working end 23 from exiting or passing beyond the sheath end 60. The "hot" end or electrode 30 in this example of the instrument can still extend beyond the end 60 of the insulating sheath 54. The sheath and instrument can then be guided along the distal ureter until reaching the bladder, dissecting or resecting tissue along its path. The sheath end 60 may optionally include a distal circumferentially rotatable end region to allow ease of 360° rotation of the instrument during resection of the bladder cusp in this example.

Once the retainer 24 reaches the bladder 48 during the nephroureterectomy procedure, the surgical component 30 can be energized and the instrument 52 rotated to dissect the ureter 44 at the bladder cusp 49.

Figure 5:
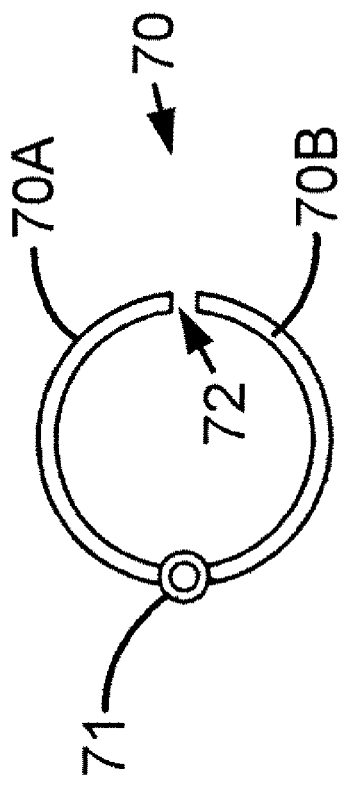
FIG. 5 shows an end view of an optional protective or insulating sheath construction.

The sheath can take on many different forms and yet perform the intended insulation and/or protective function. FIG. 4 shows an end view of the sheath 54 depicted in FIG. 3. The sheath 54 is a flexible plastic material with an elongate longitudinal slit 66. FIG. 5 depicts a two-part sheath 70 with a hinge 71 positioned opposite an elongate slit 72. The two clamshell halves 70A and 70B can be pivoted away from one another to open a gap at the slit 72 for attachment of the sheath to a target structure 44. The sheath 70 can then be manipulated to close the gap at the slit 72. If desired, one or more clamps or other devices (not shown) can be utilized on the sheath to retain the sheath in the closed position.

Figure 6:
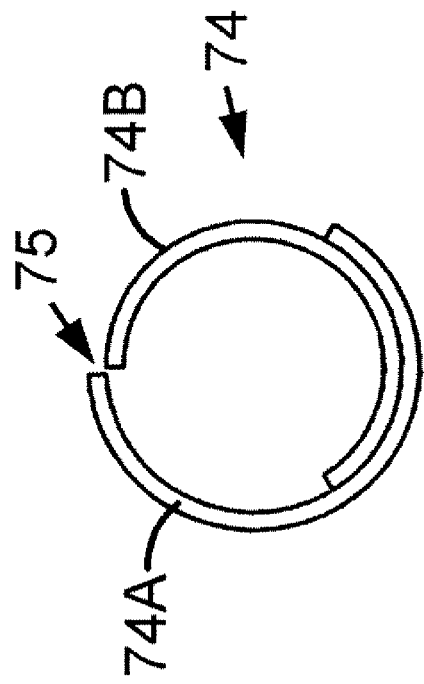
FIG. 6 shows another optional protective or insulating sheath construction.

FIG. 6 illustrates another one of many possible examples of a sheath 74. In this example, the sheath 74 includes two elongate C-shaped sections 74A, 74B, with one section being nested within the other and slidably rotatable relative to the other. The two sheath components 74A, 74B can be slidingly rotated about the longitudinal axis to open a gap at a slit 75. When the sheath 74 is in place, the two components 74A, 74B can be rotated to a closed position closing the slit 75 and, again, can be locked or secured utilizing one or more clamping or locking devices (not shown), if desired.

During the nephroureterectomy procedure, it is desirable to remove the entire ureter, leaving no tissue behind. The disclosed sheaths 54, 70, and 74 can provide insulation from the electrocautery or electric or other energized surfaces of the surgical component 30 of the retainer 24. In each example, the sheath can be formed of a relatively firm material so that it protects the structure of the target tissue from damage and inadvertent dissection, but yet can flex for ease of installation.

The retainer 24 or working end configuration can vary from the disclosed helical shape described previously. In one example shown in FIG. 7, an optional retainer can be a loop or annular ring 80 connected to the distal end 23 of the shaft 22 of a surgical instrument 82. In this example, the ring 80 has a center axis 'R' arranged perpendicular to a plane of the ring 80. The interior of the ring forms the tissue holding space 84. In this example, to eliminate interference with the shaft 22 of the instrument 84, the shaft can be connected at a circumferential edge of the ring 80 so that the shaft longitudinal axis 'A' is laterally offset from the axis 'R' of the ring. Surgical components 86 are shown extending longitudinally from the ring 80 in a direction opposite to the shaft 22. The components, 86 in this example represent an alternative bipolar electrode arrangement. In this example, when rotated, the electrodes 86 will effectively rotate about the axis 'R' of the ring 80 and circumvent the target structure 44 supported within the tissue holding space 84 to dissect the target structure from an adjacent organ or tissue.

To install the ring 80 on a target structure 44, the ring can include a separation (not shown) so that the ring can be opened and installed. This can be done in a manner similar to one any one of the sheaths described previously. Alternatively, the ring 80 can be a closed or fixed loop and installed on a target structure that is first cut transversely. The ring can be slipped over an exposed cut end of the target structure 44 and then guided along that portion of the structure.

The disclosed surgical instruments may also employ optional, additional surgical devices and features. In one example, an optional device can either be provided as a separate device from the disclosed instruments, or provided as a component carried by the instruments. One such supplemental device can be provided to grasp and advance the dissecting instrument along the target structure. The disclosed surgical instruments may employ a suction device or vacuum cup surrounding the retainer. When inserted in a patient, suction can be utilized to help grasp and hold adjacent tissue during the electrocautery or other dissection procedure. The surgical instruments disclosed herein may also contain an additional stapling device to close an area that has been cut or resected. Such a stapling device can also be utilized to staple closed an organ or other tissue after a target structure or tissue is resected, such as closing the bladder after resection of the ureter.

The particular surgical device examples disclosed herein are highly suitable for nephroureterectomy procedures. However, similar devices could be formed and used for dissecting, resecting, or sparing an artery, vein, nerve, or other target tissue or structure. During a nephroureterectomy procedure, as the ureter continues into the bladder, the surgical devices disclosed herein can resect the adjacent bladder tissue, including muscle and mucosa, and remove all tissue including part of the bladder mucosa surrounding the ureteral meatus. After resection, a stapling device, whether part of the surgical instruments disclosed herein or a separate component, may be used to grasp and staple the opening in the bladder.

A modification to the disclosed surgical procedure can include placing a ureteral catheter with a balloon or hard expandable disk on its distal end internal to the ureter and/or the bladder. The catheter can be utilized to apply traction on the bladder at the point at which the ureter enters the bladder. This can aid in extending or distending the tissue surrounding the ureter at the bladder cusp up against the surgical components disclosed herein.

The instruments disclosed herein are not intended to be limited to any particular materials for construction of the various components. The insulating materials for the shaft exterior and the sheath are well known. Plastic, thermoplastic, or rubber compositions, or combinations of such materials can be utilized. Similarly, the thicker insulation or protective material on the retainer end in the first example described above can also vary. The end can be dip coated, sprayed, or covered with a flexible sleeve to form the protective or insulating layer. That layer can also be a plastic, a thermoplastic, or a rubber composition or the like.

Although certain surgical instruments and methods have been described herein in accordance with the teachings of the present disclosure, the scope of coverage of this patent is not limited thereto. On the contrary, this patent covers all embodiments of the teachings. of the disclosure that fairly fall within the scope of permissible equivalents.

What is claimed is:

1. A surgical instrument comprising:
   an elongate shaft having a longitudinal shaft axis, a proximal grip end, and a distal working end, the shaft being rotatable about its longitudinal axis by user manipulation of the proximal grip end;
   an energy source coupled to the surgical instrument;
   a tissue retainer positioned at the distal working end of the shaft and rotatable with the shaft, the retainer having a curved portion that lies in a plane that extends around a retainer axis between a first end and a second end with the retainer axis being perpendicular to the plane in which the curved portion lies, a tissue holding space within the curved portion, and the first and second ends of the curved portion being spaced to define an entry opening into the holding space, the retainer configured to be received over and at least partly circumvent a target structure of a surgical field received in the holding space via the entry opening; and
   an elongated surgical dissection component depending from the retainer generally parallel to but laterally offset from the retainer axis and rotatable with rotation of the shaft and retainer, the surgical dissection component being the only section of the surgical instrument selectively energizeable by the energy source to dissect selected tissue contacting the surgical instrument.

2. A surgical instrument according to claim 1, wherein the surgical component is a monopolar electrode tip extending from a portion of the retainer, and wherein the shaft is metallic and coupled to an electrical energy source that delivers current to the monopolar electrode when the electrical energy source is energized.

3. A surgical instrument according to claim 1, wherein the surgical component is bipolar and has a pair of electrode tips on the retainer circumferentially spaced apart around the retainer axis of the tissue holding space, and wherein the energy source is an electrical energy source coupled to each of the electrode tips.

4. A surgical instrument according to claim 1, wherein the retainer is a wire formed in a helical configuration and circumferentially spiraling greater than 180 degrees around the tissue space, the entry opening defined between spaced apart portions of the wire of the retainer.

5. A surgical instrument according to claim 4, wherein at least surface regions of the wire retainer that face inward into the tissue space are insulated.

6. A surgical instrument according to claim 5, wherein the wire retainer is coated with an insulating material.

7. A surgical instrument according to claim 1, wherein the energy source is one of an electrical, laser, radiofrequency, microwave, or ultrasonic energy source.

8. A surgical instrument according to claim 1, wherein the retainer is an annular ring that is openable to create the entry opening and closable to completely circumvent the tissue space.

9. A surgical instrument according to claim 8, wherein the retainer axis defined by the annular ring is radially offset but generally parallel to the longitudinal axis of the shaft.

10. A surgical instrument according to claim 1, wherein the retainer axis of the guide section and tissue space and the longitudinal axis of the shaft are co-linear with one another.

11. A surgical instrument according to claim 1, wherein the cutting element is radially offset from the retainer axis and the longitudinal axis.

12. A surgical instrument according to claim 1, wherein the shaft axis and the retainer axis are generally parallel to one another.

13. A surgical instrument for ureter dissection, the surgical instrument comprising:
   an elongate shaft having a longitudinal shaft axis, a proximal grip end, and a distal working end, the shaft being rotatable about its longitudinal axis by user manipulation of the proximal grip end;
   an electrical current source coupled to the surgical instrument and selectively actuable by the user;
   a spiral retainer positioned at and extending from the distal working end of the shaft and rotatable with the shaft, the spiral retainer extending helically around a retainer axis and forming a tissue holding space within the spiral retainer and an entry opening into the holding space between longitudinally adjacent portions of the spiral retainer, the spiral retainer configured to be received over and circumvent a target structure of a surgical field received in the holding space via the entry opening; and
   an elongated electrode electrically coupled to the electrical current source and depending from the retainer generally parallel to but laterally offset from the retainer axis, the electrode being rotatable with rotation of the shaft and the spiral retainer, the electrode being the only section of the surgical instrument selectively energizeable as the electrically current source is actuated to dissect selected tissue contacting the surgical instrument, the surfaces of the spiral retainer, other than the electrode, being covered by a protective electrically insulating material.

14. A surgical instrument according to claim 13, further comprising:
   a pair of the electrodes, each coupled by a separate wire to the electrical current source and configured to form a bipolar surgical component.

* * * * *